United States Patent [19]
Bland et al.

[11] Patent Number: 6,071,580
[45] Date of Patent: Jun. 6, 2000

[54] ABSORBENT, EXTRUDED THERMOPLASTIC FOAMS

[75] Inventors: David G. Bland, Midland; William G. Stobby, Mt. Pleasant; Gene D. Rose, Midland; Steve W. Mork, Midland; Thomas L. Staples, Midland; Gordon D. McCann, Midland, all of Mich.

[73] Assignee: The Dow Chemical Company, Midland, Mich.

[21] Appl. No.: 09/096,029

[22] Filed: Jun. 11, 1998

Related U.S. Application Data

[60] Provisional application No. 60/049,181, Jun. 11, 1997.

[51] Int. Cl.$^7$ .......................... B29D 22/00; A61F 13/15; C08J 9/00
[52] U.S. Cl. ............................ 428/36.5; 521/74; 521/79; 521/142; 428/34.1; 428/34.3; 428/34.8; 428/35.7; 604/369; 604/370; 604/372
[58] Field of Search ................................ 521/74, 79, 142; 428/34.1, 34.3, 34.8, 35.7, 36.5; 604/369, 370, 372

[56] References Cited

U.S. PATENT DOCUMENTS

| | | | |
|---|---|---|---|
| 5,260,345 | 11/1993 | DesMarais et al. | 521/148 |
| 5,338,766 | 8/1994 | Phan et al. | 521/63 |
| 5,573,994 | 11/1996 | Kabra et al. | 502/402 |
| 5,618,853 | 4/1997 | Vonken et al. | 521/60 |

FOREIGN PATENT DOCUMENTS

| | | |
|---|---|---|
| 2129278 | 8/1994 | Canada . |
| 02076715 A2 | 3/1990 | Japan . |
| 02120339 | 5/1990 | Japan . |

OTHER PUBLICATIONS

Derwent Abstract No. 83–784429/41 to EP 090.507A.

*Primary Examiner*—Samuel A. Acquah

[57] ABSTRACT

Disclosed is an absorbent, extruded, open cell thermoplastic foam. The foam has an open cell content of about 50 percent or more and an average cell size of up to about 1.5 millimeters. The foam is capable of absorbing a liquid at about 50 percent or more of its theoretical volume capacity when absorbing a liquid. The foam preferably has an average equivalent pore size of about 5 micrometers or more. The foam preferably has a structure substantially of cell walls and cell struts. Further disclosed is a method for absorbing a liquid employing the foam by elongation of the extrudate of the extrusion die. Further disclosed is a method of enhancing absorbency of an open cell foam by applying a surfactant to an exposed surface of the foam such that it remains at the surface and does not infiltrate a substantial distance into the foam. Further disclosed is a meat tray and a diaper containing the foam.

46 Claims, 9 Drawing Sheets

ABSORBENT, EXTRUDED THERMOPLASTIC FOAMS

This application claims the benefit of U. S. Provisional Application Ser. No. 60/049,181 filed Jun. 11, 1997.

BACKGROUND OF THE INVENTION

The prior art relates various foams which can be employed in absorbency applications. Two varieties are high internal phase emulsion (HIPE) foams and extruded, open-cell thermoplastic foams. HIPE foams are seen by example in U.S. Pat. Nos. 5,372,766 and 5,387,207 and extruded, open-cell thermoplastic foams are seen by example in Canadian Patent Application 2,129,278 and Japan Application No. 2-120339.

HIPE foams are formed by the cross-linking polymerization of hydrophobic monomers as the continuous phase of a water-in-oil emulsion in which the water phase comprises at least 70 weight percent and typically greater than 95 weight percent. The structure of HIPE foams depends on their composition and process for making, but the most desirable ones for absorbing large amounts of fluid are substantially open-cell with thin cell walls containing numerous pores therein in communication with neighboring cells. HIPE foams can be prepared which exhibit relatively high absorption rates and have absorption capacities of greater than 25 grams of water per gram of foam. Thus, HIPE foams are very useful in absorbing fluids. HIPE foams are costly, however, due to the large volumes of water used in their preparation.

Extruded, open-cell thermoplastic foams typically have substantially more internal structure than HIPE foams. They typically are formed of interconnecting struts and walls with the open cell character being derived from a relatively small number of small diameter pores within relatively thick cell walls. Struts are formed by the intersection of cell walls. The relatively substantial internal cell structure and small pores in the cell walls induce viscous drag and resistance to flow within the foam. The relatively thick cell walls reduce the amount of fluid that can be absorbed within the foam. The relatively small number of small diameter pores may result in some portions of the foam not being accessible to the absorption of fluid. Thus, prior art extruded, open-cell foams, even those of essentially 100 percent open-cell content, typically exhibit both relatively low absorption capacity and a relatively low slow absorption rate.

It would be desirable to have an extruded, open-cell thermoplastic foam which exhibited both high absorption capacity and high absorption rate. It would also be desirable if absorption rate could be enhanced in specific directions or dimensions within the foam.

SUMMARY OF THE INVENTION

According to one aspect of the present invention, there is an extruded, open-cell thermoplastic foam. The foam has an open-cell content of about 50 percent or more and an average cell size of up to about 1.5 millimeters. The foam is capable of absorbing a liquid at about 50 percent or more of its theoretical volume capacity. The foam preferably has an average equivalent pore size of about 5 micrometers or more. The foam preferably has a structure substantially of cell walls and cell struts.

According to another aspect of the present invention, there is a process for making an extruded open-cell thermoplastic foam of about 50 percent or more open cell content. The process comprises extruding and expanding an expandable thermoplastic gel comprising a mixture of a thermoplastic material and a blowing agent out of an extrusion die to form an expanding extrudate which expands to form the foam. The extrudate is elongated as it exits the extrusion die and expands to an extent sufficient to make the average cell size about 25 percent or more larger in the dimension of elongation than the average cell size in either or both of the other dimensions.

According to another aspect of the present invention, there is a method for enhancing the absorbency of an open cell foam, comprising: a) providing the foam, b) applying a surfactant to an exposed surface of the foam such that the surfactant remains at the surface and does not infiltrate a substantial distance into the foam. Preferably, the surfactant is applied in a solution form and subsequently permitted to dry to leave a residue on the exposed surface. The surfactant solution may be permitted to dry by evaporation or by application of heat.

According to another aspect of the present invention, there is a method for absorbing a liquid wherein the present foam is contacted with the liquid such that the liquid is absorbed.

According to another aspect of the present invention, there is a meat tray capable of receiving and retaining meat therein, comprising: a tray and an insert, the insert is comprised of the extruded, open-cell foam described above and is positioned within the tray.

According to another aspect of the present invention, there is a diaper suitable for bodily use. The diaper comprises a sheet foam having an open cell content of about 50 percent or more and an average cell size of up to about 1.5 millimeters. The foam has a structure of substantially cell walls and struts and is capable of absorbing liquid at about 50 percent or more of its theoretical volume capability.

DETAILED DESCRIPTION

Figure 1:
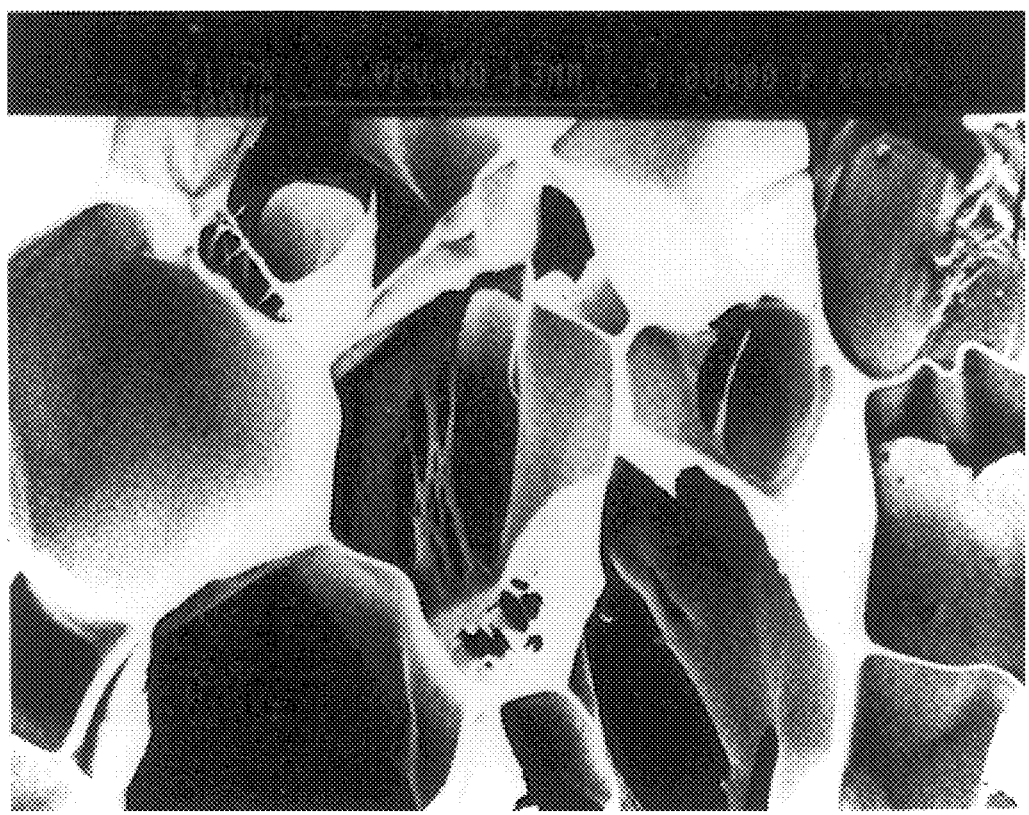
FIG. 1 is a photomicrograph of a cross-section of an absorbent foam taken by scanning electron microscopy. The photomicrograph was taken at a magnification of 71.7. The foam has an average cell size of 200–300 micrometers. The foam is useful in the present invention.
Figure 2:
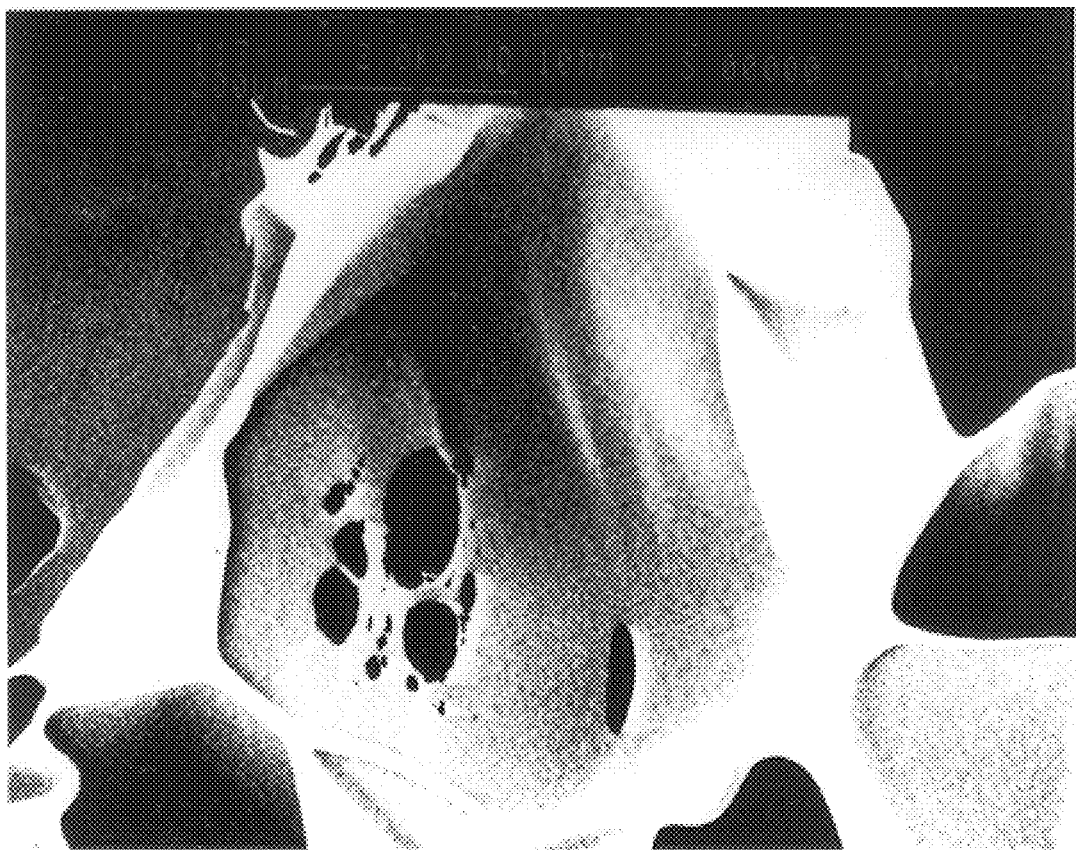
FIG. 2 is a photomicrograph of a cross-section of an absorbent foam taken by scanning electron microscopy. The photomicrograph was taken at a magnification of 113. The foam has an average cell size of 200–300 micrometers. The foam is useful in the present invention.
Figure 3:
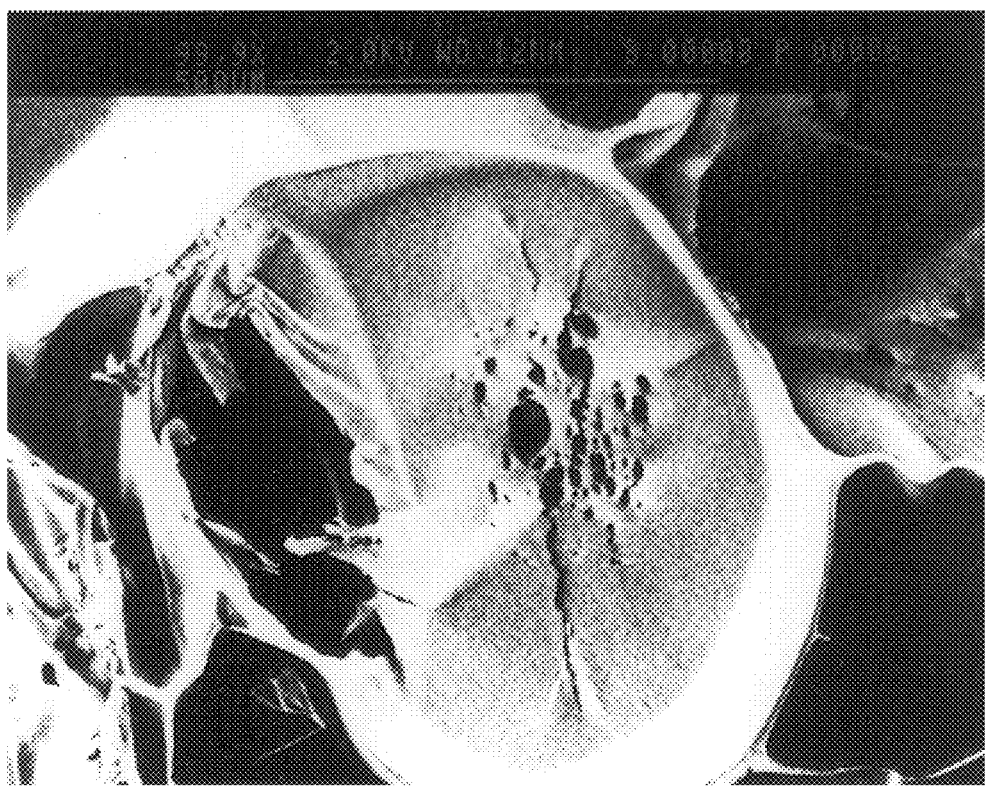
FIG. 3 is a photomicrograph of a cross-section of an absorbent foam taken by scanning electron microscopy. The photomicrograph was taken at a magnification of 99.9. The foam has an average cell size of 200–300 micrometers. The foam is useful in the present invention.
Figure 4:
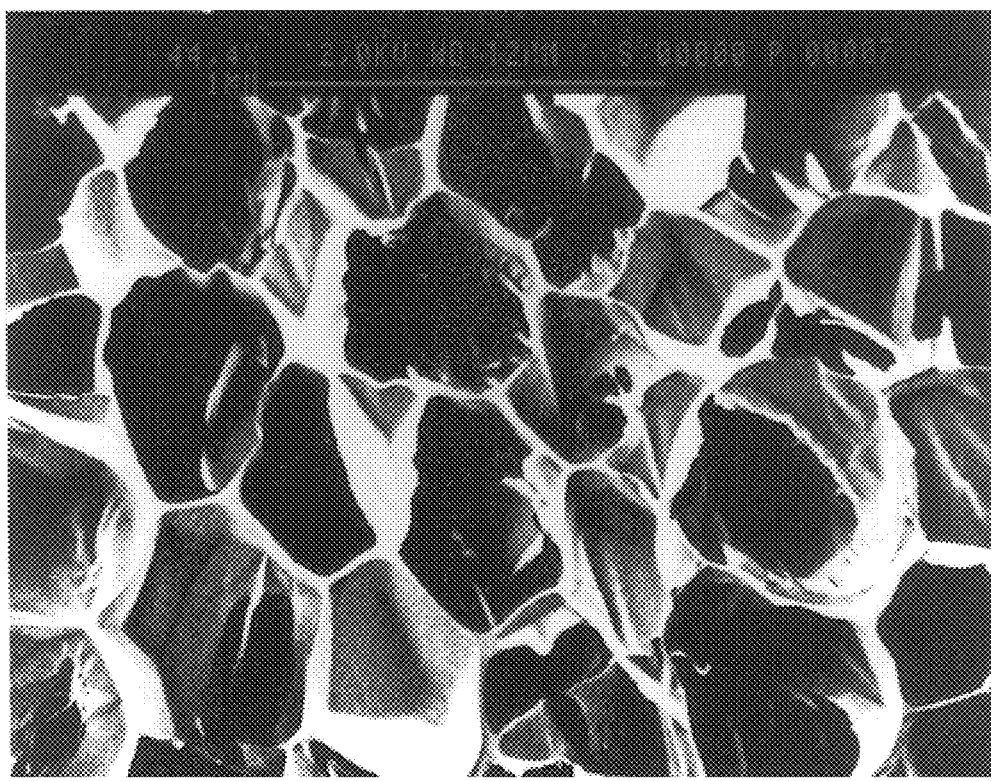
FIG. 4 is a photomicrograph of a cross-section of an absorbent foam taken by scanning electron microscopy. The photomicrograph was taken at a magnification of 44.4. The foam has an average cell size of 200–300 micrometers. The foam is useful in the present invention.
Figure 5:
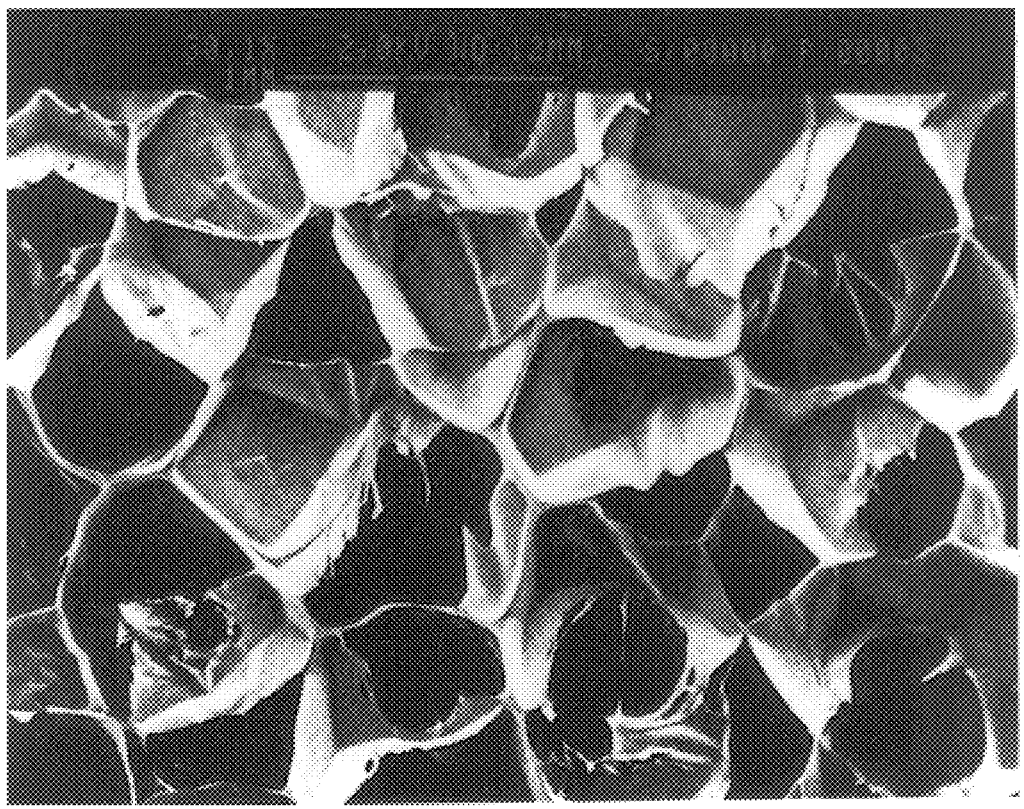
FIG. 5 is a photomicrograph of a cross-section of an absorbent foam taken by scanning electron microscopy. The photomicrograph was taken at a magnification of 30.1. The foam has an average cell size of 200–300 micrometers. The foam is useful in the present invention.

The extruded, open-cell thermoplastic foams of the present invention exhibit excellent and unexpected absorptive properties and characteristics.

The present foams differ from the prior art extruded, open cell foams in their unique structure. The present foams have a substantially cell wall/cell strut structure yet exhibit a larger ratio of effective average pore size relative to the average cell size than prior art foams. Prior art extruded open cell foams, even those with relatively high levels of open cell content, i.e. 90–100 percent, have relatively small pores within their cell walls and limited pore incidence level throughout the foam. The relatively small pores and limited pore incidence level result in relatively slow absorption rate and relatively low absorption capacity due to viscous drag and resistance to flow.

Though not bound by any particular theory, the larger ratio of effective average pore size relative to the average cell size may result from any or a combination of the following: cell walls having larger pores therein, a larger proportion of cell walls having pores therein, a larger proportion of cell walls generally vertical and horizontal to the extrusion direction having pores therein, and a minor proportion of cell walls missing in the cellular structure. Generally, the size of pores and/or their incidence level and/or the proportion of cell walls generally vertical and horizontal to the extrusion direction having pores therein and/or the proportion of cell walls missing in the cellular structure in the present foam is greater than for prior art extruded, open cell foams of substantially equivalent cell size and open cell content.

The lower viscous drag and resistance to liquid flow of the present foam enables its substantial internal cell wall/cell strut structure to be utilized to advantage instead of disadvantage. The substantial internal structure of extruded foams affords a relatively high internal surface area to foam volume ratio. The relatively high internal surface area to foam volume ratio of extruded foams affords the potential of high absorption rate and capacity when there is relative compatibility between the material comprising the foam and the liquid to be absorbed. However, when the ratio of effective average pore size to average cell size is relatively small as in the prior art extruded, open cell foams, viscous drag and resistance to flow denudes or substantially diminishes the potentially positive impact of the substantial internal cell wall/cell strut structure. The present foam has a ratio of effective average pore size to average cell size great enough to substantially diminish viscous drag and resistance to liquid flow such that the potentially high absorption rate and capacity afforded by the substantial internal cell wall/cell strut structure can be realized. The potentially high absorption rate and capacity is realized with the present foam when there is relative compatibility, i.e. a contact angle of 90 degrees or less, between the thermoplastic material comprising the internal surfaces of the foam and the liquid to be absorbed.

The present foam has an open cell content of about 50 percent or more, preferably about 70 percent or more, more preferably about 90 percent or more, and most preferably about 95 percent or more according to ASTM D2856-A. The present foam preferably has an average cell size of about 1.5 millimeters or less and preferably about 0.01 to about 1.0 millimeters according to ASTM D3576-77. One useful foam embodiment has an average cell size of about 0.2 to about 0.7 millimeters according to ASTM D3576-77. Another useful foam embodiment has an average cell size of about 0.01 to about 0.07 millimeters according to ASTM D3576-77. A particularly useful polystyrene foam is one having an average cell size of about 0.04 to about 0.06 millimeters according to ASTM D3576-77.

The present foam preferably further has an equivalent average pore size of about 5 micrometers or more, preferably about 10 micrometers or more, and most preferably about 15 micrometers or more. Average cell size and equivalent average pore size differ in that average cell size relates to average cell dimension in the foam and equivalent average pore size relates to average pore dimension within or through cell walls of the cells of the foam. Equivalent average pore size is determined according to the method described below.

The present foam has a density of preferably from about 16 to about 250 kilograms per cubic meter ($kg/m^3$) and more preferably from about 25 to about 100 $kg/m^3$ according to ASTM D- 1622-88.

The present foam is capable of absorbing about 50 percent or more, preferably about 70 percent or more, and most preferably about 90 percent or more of its theoretical volume capacity. Theoretical volume capacity is the volume of liquid absorbed per unit weight of foam and is commonly described in units of cubic centimeters of liquid per gram of foam. Theoretical volume capacity (TVC) is calculated according to the following:

$$TVC=(1/\rho_f) \times (1-\rho_f/\rho_p) \times (\% \text{ o.c.}/100)$$

wherein $\rho_f$=foam density $\rho_p$=polymer density

% o.c.=percent open cell content according to ASTM D2856-A

Volume percent absorbed is determined by submersing a foam of 5 millimeter thickness under 1 inch (2.5 centimeters) of a liquid for 4 hours at atmospheric pressure. The skin layer of the foam is preferably removed prior to submersion of the foam. A useful liquid for purposes of measurement will have a contact angle of 90 degrees or less with respect to the internal surfaces of the foam. When testing the TVC of a polystyrene foam, a useful liquid is an aqueous (water) detergent solution which exhibits the indicated contact angle range with respect to the internal surfaces of the foam.

The foam exhibits superior liquid retention under load (under weight load or other externally induced pressure) Preferably, the foam can withstand pressures of 30 pounds per square inch (210 kilopascals) with loss of less than 10 percent of its retained liquid.

The foam may take any physical configuration known in the art such as sheet or plank. Desirable sheet foams include those less than 0.375 inch (0.95 cm) in thickness in cross-section. Desirable plank foams include those having in cross-section thickness of 0.375 inch (0.95 cm) or more. Useful sheet foams can be made by skiving or slicing of plank foams into two or more plies or by extrusion through an annular or slit die. Desirably, the closed cell skin of the foam formed upon extrusion is skived, sliced, or scraped off.

It is possible to increase the rate of absorption mechanically by perforating the foam with needles or other sharp, pointed objects or by compressing it. The excellent absorptive performance of both relatively large average cell size and relatively large pore size can be attained. The foam may be perforated or non-perforated.

FIGS. 1–5 are photomicrographs of cross-sections of absorbent foams taken by scanning electron microscopy. The foams are useful in the present invention. Foam cells having pores within their cell walls and/or having a minor proportion of cell walls missing are seen in the figures. In those figures where certain cell walls are missing, the foams retain a substantially cell wall/cell strut structure.

Extruded thermoplastic foams are generally prepared by heating a thermoplastic material to form a plasticized or melt polymer material, incorporating therein a blowing agent to form a foamable gel, and extruding the gel through a die to form the foam product. Prior to mixing with the blowing agent, the polymer material is heated to a temperature at or above its glass transition temperature or melting point. The blowing agent may be incorporated or mixed into the melt polymer material by any means known in the art such as with an extruder, mixer, blender, or the like. The blowing agent is mixed with the melt polymer material at an elevated pressure sufficient to prevent substantial expansion of the melt polymer material and to generally disperse the blowing agent homogeneously therein, an optional nucleating agent may be blended in the polymer melt or dry blended with the polymer material prior to plasticizing or melting. The foamable gel is typically cooled to a lower temperature to optimize or attain desired physical characteristics of the foam. The gel may be cooled in the extruder or other mixing device or in separate coolers. The gel is then extruded or conveyed through a die of desired shape to a zone of reduced or lower pressure to form the foam. The zone of lower pressure is at a pressure lower than that in which the foamable gel is maintained prior to extrusion through the die. The lower pressure may be superatmospheric or subatmospheric (evacuated), but is preferably at an atmospheric level. As the extrudate exits and expands from the die, the foam is elongated by mechanical means to assist in pore formation and open cell formation. Elongation is discussed below.

To assist in extruding open-cell thermoplastic foams, it may be advantageous to employ a polymer different than the predominant polymer employed in the thermoplastic material. Employing a minor amount of a polymer different than the predominate polymer enhances open cell content development. For example, in making a polystyrene foam, minor amounts of polyethylene or ethylene/vinyl acetate copolymer may be employed. In making a polyethylene foam, minor amounts of polystyrene may be employed.

Formation of extruded open-cell thermoplastic foams of the desired elevated levels of average open cell content and equivalent average pore size can be enhanced by elongating extrudate as it exits and expands from the extrusion die. Formation of foams by elongation is not required but is preferred.

Elongation can increase the relative proportion of cell walls having pores therein and/or increase the average size of existing pores. Equivalent average pore size can be significantly increased. Thus, even extruded foams which exhibit very high open content, i.e. 95 percent or more, without elongation can have their absorptive properties, including wicking rate and absorption capacity, significantly enhanced by elongation because the proportion of cell walls having pores therein and/or the average cell size of existing pores is increased.

Elongation is best accomplished by mechanically elongating the extrudate as it emerges and expands from the extrusion die. Elongation can occur when a substantial portion of the thermoplastic material comprising the extrudate is at a temperature is soft or elastic. For a substantially amorphous thermoplastic material, this temperature will be in the vicinity of the glass transition temperature range. For a substantially crystalline thermoplastic material, this temperature will be in the vicinity of the crystalline melting point. The extrudate will cool as it expands and ultimately cool to a temperature at which it will no longer elongate.

Elongation of the extrudate renders foam cells more elongated dimensionally in the direction of elongation than they would be without the elongation. Elongation further results in the foam cells being reduced in dimension in the two dimensions perpendicular to the direction of elongation than they would be without the elongation. For instance, elongation in the extrusion direction renders foam cells larger in dimension in the extrusion direction but smaller in dimension in the vertical and horizontal directions than they would be without the elongation. The larger the average foam cell size, the greater the extent of elongation possible because the cell walls will be thicker on the average and will tend to cool more slowly than the thinner cell walls of foam cells of smaller average cell size.

In addition to altering the dimensions of the foam cells, elongation tends to make thinner cell walls directional to the force of elongation, and thus, more likely to develop pores in those cell walls and/or make existing pores larger than they might be without elongation. For instance, elongation in the extrusion direction renders cell walls thinner in the horizontal (transverse) direction and the vertical direction. Thus, pores are more likely to develop and/or be larger in the horizontal and vertical directions than without elongation. Elongation in the horizontal (transverse) direction renders cell walls thinner in the extrusion direction and the vertical direction. Thus, pores are more likely to develop and/or be larger in the extrusion and vertical directions than without elongation.

The wicking rate of a fluid into the foam is significantly enhanced by the presence of the additional pores and/or larger pores. Elongation can be used to enhance the wicking rate of a liquid into the foam in a certain direction or directions. Vertical and horizontal wicking rates can be enhanced by elongation in the extrusion direction. Wicking rate in the extrusion direction can be enhanced by horizontal or transverse elongation.

The extrudate can be elongated to an extent necessary to result in an expanded, stable foam having an average cell size of about 25 percent or more larger in any dimension compared to the average cell size in either or both of the other two dimensions. For instance, the average cell size in the extrusion dimension can be about 25 percent or more larger compared to the average cell size of either or both of the vertical dimension and the horizontal dimension. Likewise, the average cell size in the horizontal or transverse dimension can be about 25 percent or more larger than the average cell size in the extrusion direction and/or the vertical dimension. Average cell size in any given dimension can be determined according to ASTM D3576-77.

The extrudate can be mechanically elongated to an extent that the extrudate does not break, tear, or introduce substantial voidage into the cell structure. The larger the cross-section of the expanding extrudate, the greater the mechanical stress which must be applied to effect the desired extent of elongation.

Figure 6:
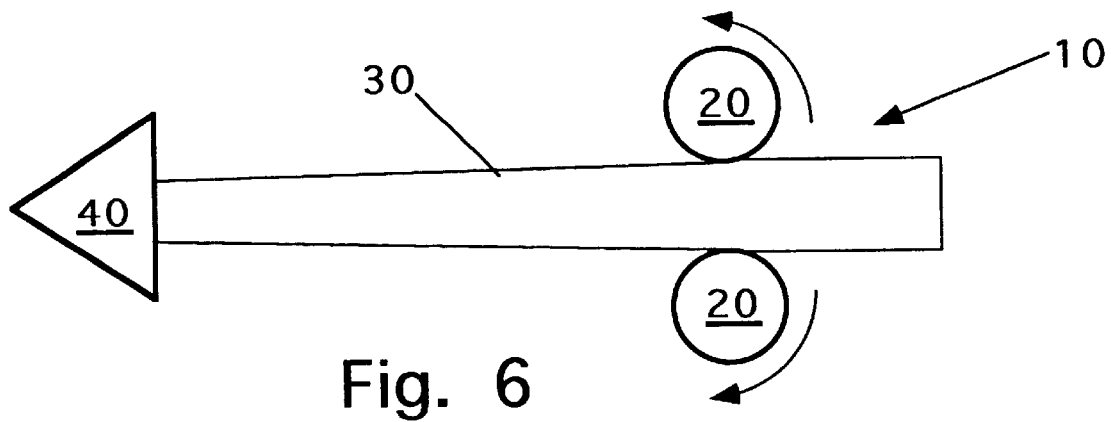
FIG. 6 is a schematic side view of an extrusion process according to the present invention.
Figure 7:
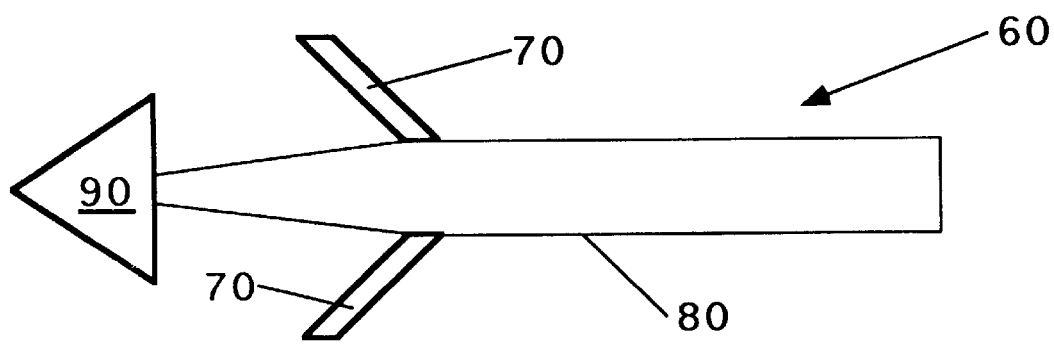
FIG. 7 is a schematic side view of another embodiment of an extrusion process according to the present invention.

Elongation can be accomplished by any of several means. For elongation in the extrusion direction, the extrudate may be stretched in the extrusion direction by a pair of opposing nip rollers or belts located downstream of an extrusion die. Such a method of elongation is seen in an elongation apparatus 10 in FIG. 6, which shows a pair of opposing rotating nip rollers 20 pulling or stretching an extrudate 30, which is exiting an extrusion die 40. Elongation in both the extrusion direction and the transverse directions may be accomplished by employing mechanical pressure on the extrudate by a pair of opposing forming plates located just downstream of the extrusion die. The extrudate is elongated in the extrusion direction between the forming plates and elongated in the transverse direction around the sides or lateral to the forming plates. FIG. 7 shows and elongation apparatus 60 with a pair of opposing forming plates 70 exerting pressure upon opposing surfaces of an extrudate 80 (above and below) exiting an extrusion die 90. For elongation horizontal or transverse to the extrusion direction, a conventional tentering apparatus (not shown) downstream of the extrusion die may be used to stretch the extrudate in that direction. Elongation can be effective with both sheet foams and plank foams but is particularly effective with sheet foams.

Although elongation is effective in producing absorptive foams of any thermoplastic material, it is particularly effective when foaming with relatively rigid thermoplastic materials such as alkenyl aromatic polymers.

The foam may be formed of any thermoplastic or blend of thermoplastics which can be formed or blown into an open cell foam of the features described herein. Useful thermoplastics include natural and synthetic organic polymers. Suitable plastics include polyolefins, polyvinylchloride, alkenyl aromatic polymers, cellulosic polymers, polycarbonates, starch-based polymers, polyetherimides, polyamides, polyesters, polyvinylidene chlorides, polymethylmethacrylates, copolymer/polymer blends, rubber modified polymers, and the like. Suitable alkenyl aromatic polymers include polystyrene and copolymers of styrene and other copolymerizable monomers.

If desired, the foam can be blown from a thermoplastic material which is partially or substantially biodegradeable. Useful polymers include cellulosic polymers and starch-based polymers.

A useful thermoplastic foam comprises an alkenyl aromatic polymer material. Suitable alkenyl aromatic polymer materials include alkenyl aromatic homopolymers and copolymers of alkenyl aromatic compounds and copolymerizable ethylenically unsaturated comonomers. The alkenyl aromatic polymer material may further include minor proportions of non-alkenyl aromatic polymers. The alkenyl aromatic polymer material may be comprised solely of one or more alkenyl aromatic homopolymers, one or more alkenyl aromatic copolymers, a blend of one or more of each of alkenyl aromatic homopolymers and copolymers, or blends of any of the foregoing with a non-alkenyl aromatic polymer. The alkenyl aromatic polymer material comprises greater than 50 and preferably greater than 70 weight percent alkenyl aromatic monomeric units. Most preferably, the alkenyl aromatic polymer material is comprised entirely of alkenyl aromatic monomeric units.

Suitable alkenyl aromatic polymers include those derived from alkenyl aromatic compounds such as styrene, alphamethylstyrene, ethylstyrene, vinyl benzene, vinyl toluene, chlorostyrene, and bromostyrene. A preferred alkenyl aromatic polymer is polystyrene. Minor amounts of monoethylenically unsaturated compounds such as $C_{2-6}$ alkyl acids and esters, ionomeric derivatives, and $C_{4-6}$ dienes may be copolymerized with alkenyl aromatic compounds. Examples of copolymerizable compounds include acrylic acid, methacrylic acid, ethacrylic acid, maleic acid, itaconic acid, acrylonitrile, maleic anhydride, methyl acrylate, ethyl acrylate, isobutyl acrylate, n-butyl acrylate, methyl methacrylate, vinyl acetate and butadiene. Useful alkenyl aromatic polymer foams may comprise substantially (i.e., greater than 90 percent by weight) or entirely polystyrene.

Preferred alkenyl aromatic polymer foams comprise polystyrene of about 125,000 to about 300,000 weight average molecular weight, about 135,000 to about 200,000, about 165,000 to about 200,000 weight average molecular weight, and about 135,000 to about 165,000 weight average molecular weight according to size exclusion chromatography. Polystyrene in these molecular weight ranges is particularly suited to forming foams, particularly elongated foams, useful in the present invention.

Useful extruded thermoplastic foams include extruded microcellular alkenyl aromatic polymer foams of high open cell content and processes for making are disclosed in WO 96/34038, which is incorporated herein by reference. The disclosed foams have an average cell size of about 70 micrometers or less and an open cell content of about 70 percent or more.

In the process disclosed in WO 96/34038, useful blowing agents include 1,1-difluoroethane (HFC- 152a), 1,1,1-trifluoroethane (HFC-143a), 1,1,1,2-tetrafluoroethane (HFC- 134a), chlorodifluoromethane (HCFC-22), carbon dioxide ($CO_2$), and difluoromethane (HFC-32). Preferred blowing agents are HFC-152a, HFC-134a, and carbon dioxide. The above blowing agents will comprise 50 mole percent or more and preferably 70 percent or more of the total number of moles of blowing agent. The balance may be made up of other blowing agents. The amount of blowing agent employed is from about 0.06 to about 0.17 gram-moles per 100 grams of polymer, preferably from about 0.08 to about 0.12 gram-moles per 100 grams of polymer, and most preferably from 0.09–0.10 gram-moles per 100 grams of polymer. The use of a relatively small amount of blowing agent allows formation of a foam with a high open cell content. Preferred foaming temperatures will vary from about 118° C. to about 160° C. Most preferred foaming temperatures will vary from about 125° C. to about 135° C. The amount of nucleating agent employed may range from about 0.01 to about 5 parts by weight per hundred parts by weight of a polymer resin. The preferred range is from 0.1 to about 3 parts by weight.

To assist in extruding open-cell thermoplastic foams, it may be advantageous to employ a polymer different than the predominant polymer employed in the thermoplastic material. Employing a minor amount of a polymer different than the predominate polymer enhances open cell content development. For example, in making a polystyrene foam, minor amounts of polyethylene or ethylene/vinyl acetate copolymer may be employed. In making a polyethylene foam, minor amounts of polystyrene may be employed. Useful teachings to preferred different polymers are seen in U.S. Ser. No. 08/880,954, which is incorporated herein by reference.

Another extruded alkenyl aromatic foam of larger average cell size and processes for making are seen in WO 96/00258, which is incorporated herein by reference. Open-cell content is about 30 percent or more according to ASTM D2856-87. The disclosed foams have a density of about 1.5 pcf to about 6.0 pcf (about 24 kg/m³ to about 96 kg/m³) and preferably a density of about 1.8 pcf to about 3.5 pcf (about 32 kg/m³ to about 48 kg/m³) according to ASTM D-1622–88. The present foam has an average cell size of from about 0.08 millimeters (mm) to about 1.2 mm and preferably from about 0.10 mm to about 0.9 mm according to ASTM D3576–77.

In the process for making the foam in WO 96/00258, the foaming temperature, which is relatively higher than that for making closed-cell foams (less than 10 percent open-cell according to ASTM D2856-87), may vary from about 118° C. to about 145° C. Foaming temperature will vary according to nucleating agent composition and concentration, blowing agent composition and concentration, polymer material characteristics, and extrusion die design. The foaming temperature for the present open-cell foam varies from about 3° C. to about 15° C. and preferably about 10° C. to about 15° C. higher than the highest foaming temperature for a corresponding closed-cell foam (less than 10 percent open-cell according to ASTM D2856-87) of substantially equivalent density and cell size made with a substantially equivalent composition (including polymer material, nucleating agent, additives, and blowing agent) in a substantially equivalent process. A preferred foaming temperature is at about 33° C. or more higher than the glass transition temperature (according to ASTM D-3418) of the alkenyl aromatic polymer material. A most preferred foaming temperature is from 135° C. to 140° C. The amount of blowing agent incorporated into the polymer melt material to make a foam-forming gel is from about 0.2 to about 5.0 gram-moles per kilogram of polymer, preferably from about 0.5 to about 3.0 gram-moles per kilogram of polymer, and most preferably from about 0.7 to 2.0 gram-moles per kilogram of polymer. A nucleating agent such as those described above may be employed. To make foams of the physical properties described in WO 96/00258 which have the pore size and pore incidence level to be effective in the present invention, it may be necessary to incorporate different polymers into the alkenyl aromatic polymer material such as polyolefins of melting temperatures of 70° C. or less, ethylene/styrene interpolymers, and styrene/butadiene copolymers or other rubbery homopolymers or copolymers.

Useful extruded, open cell thermoplastic foams include those made of styrene/ethylene interpolymers and blends of such interpolymers with alkenyl aromatic polymers and ethylene polymers described in U.S. Pat. No. 5,460,818, WO 96/14233, and U.S. Ser. No. 60/078091, filed Mar. 16, 1998, all of which are incorporated herein by reference. Such interpolymers are particularly useful in making foams having an average cell size of greater than 100 micrometers.

Open cell content and equivalent average pore size can be further enhanced by extruding a foam with a loading of a particulate water-soluble polymer such as methyl cellulose. The particulate polymer can subsequently be washed from the foam matrix by exposure to water or steam. Voids will remain in the foam matrix.

The foam may be non-crosslinked or lightly crosslinked. Non-crosslinked means the foam is substantially free of cross-linking or has the slight degree of cross-linking which may occur naturally without the use of cross-linking agents or radiation. Non-crosslinked foams contain no more than 5 percent gel per ASTM D2765-84, Method A. Lightly crosslinked foams are those having greater than 5 percent gel but less than about 25 percent gel according to the same test.

The present foams may be treated to render the internal cell surfaces of the foam more compatible with respect to a liquid to be absorbed. For example, internal cell surfaces can be rendered more hydrophillic to increase absorption of aqueous liquids such as urine or blood. Likewise, internal cell surfaces can be rendered more hydrophobic to increase absorption of oily liquids or organic liquids. To increase absorption of aqueous liquids, the internal surfaces of the foams may be sulfonated or surface treated with a surfactant. To render a foam more hydrophillic, foams may be sulfonated by exposure to sulfurous gases or liquids such as sulfur dioxide, sulfur trioxide, or sulfuric acid. The foams are then neutralized. Surfactants may be applied by soaking and infiltrating a substantial portion of or the entire foam with a solvent/surfactant solution such as an aqueous detergent or soap solution followed by drying to remove the solvent (water in the case of an aqueous solution). When a solution is applied, the exposed surface is subsequently dried by evaporation at ambient conditions or normal post-extrusion processing conditions or by heating to leave a residue of the surfactant. Heating may be accomplished by any conventional means such as by heated air, infrared heating, radiofrequency heating, or induction heating. The surfactant remains as a residue on the internal surfaces of the foam.

In the present invention, wicking rates were observed to be the fastest for foams about 70 micrometers average cell size and 15 micrometers equivalent average pore size.

In one aspect of the invention, it was found surprisingly that treating one or more exposed surfaces of the foam with a surfactant to alter the contact angle of the foam was substantially as effective as treating the entire foam in enhancing the absorbency of the foam if absorption occurs through a treated surface. The surfactant may be applied by any means known in the art such as by brushing or spraying in the form of a solvent/surfactant solution on the exposed surface or the surfactant by itself if it has a fluid consistency. When applying a water-soluble surfactant, an aqueous solution is preferred. Although not preferred, it is also possible to apply a surfactant in a powder or solid form to the surface. The surfactant is applied so that it does not infiltrate a substantial distance into the foam and remains at the treated surface and portions of the foam contiguous to the treated surface. When a solution is applied, the exposed surface is subsequently dried by the means discussed above or the water or solvent is allowed to evaporate to leave a residue of the surfactant. During absorption, the liquid is drawn or absorbed through the treated exposed surface and the surfactant residue dissolves into the liquid rendering it more compatible with the thermoplastic material comprising the foam. The compatibilized liquid then is more readily absorbed and distributed within the portions of the foam where the surfactant residue was not present. This aspect of the invention of treating one or more exposed surfaces of a foam with a surfactant can also be employed in HIPE foams, such as those disclosed in U.S. Pat. Nos. 5,372,766 and 5,387,207, which are incorporated herein by reference.

It is also possible to regulate the contact angle of the internal cell surfaces of a foam by incorporation of a surfactant into the thermoplastic material comprising the foam as the foam is being made. For extruded foams, the surfactant can be dry-blended with the thermoplastic material or melt injected into a melt of the thermoplastic material prior to extrusion through the die. Useful surfactants and methods of incorporation are seen in Canadian Patent Application 2,129,278, which is incorporated herein by reference.

The term "surfactant" as used herein describes any substance which might be applied to the cell surfaces of the foam to render them more compatible (reduce the contact angle) with respect to a particular liquid or fluid to be absorbed. The surfactant could be used to render the thermoplastic material comprising the substrate more hydrophilic or, conversely, more hydrophobic. Useful surfactants include cationic, anionic, amphoteric, and nonionic surfactants. Useful anionic surfactants included the alkylsulfonates.

Figure 10:
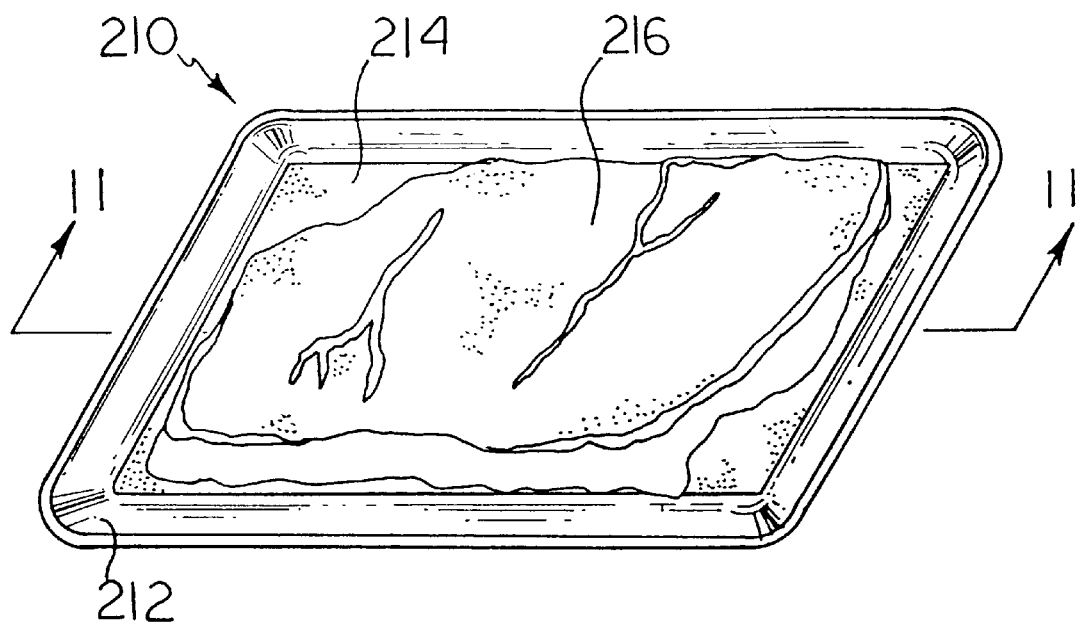
FIG. 10 is a perspective view of a meat tray of the present invention wherein the meat tray has meat therein.
Figure 11:
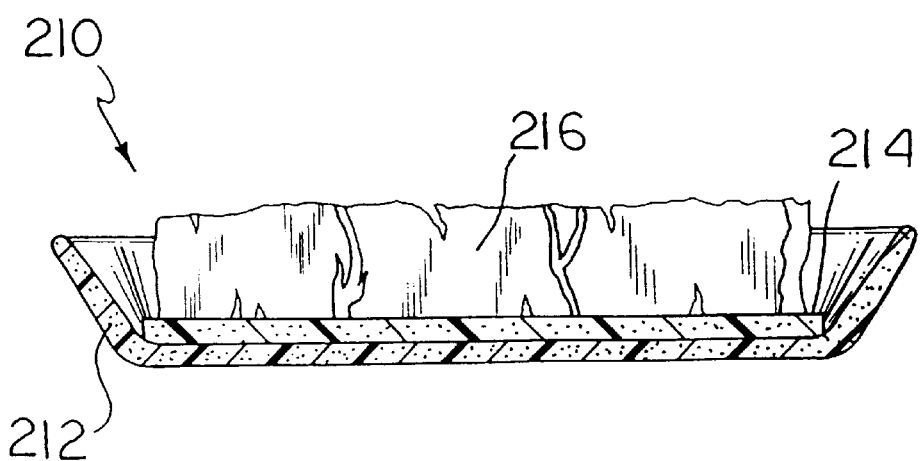
FIG. 11 is a cross-section of the meat tray of FIG. 4 along a line 6—6.

The present foam is useful in a variety of absorbency applications such as in food or barrier packaging, industrial and hydraulic oil capture and absorption, cleaning, and baby or adult diapers for bodily use. Sheet foam is particularly adapted to being fashioned, cut, or formed into diapers. Sheet foam is also particularly adaptable to being thermoformed or otherwise molded and shaped into meat trays or other food packaging forms. The sheet foam is also particularly adaptable to being employed as an insert or absorbent pad in a meat tray. A meat tray of the present invention is shown in FIGS. 10–11. Meat tray 210 comprises a closed cell plastic foam tray 212 and an extruded, open-cell foam insert 214 situated therein. Meat 216 is situated within bottom tray 212 on top of insert 214. If desired, a bottom tray may be fabricated from a material different than a foam such a paper-based material such as cardboard or linerboard or a non-foamed plastic material. If it is a foam as in the case of bottom tray 212, it typically has a much lower open cell content than the foam insert. The bottom tray and insert are preferably manufactured separately with the insert being placed in the receiving portion of the bottom tray. Optionally, an adhesive may be used to adhere the insert to the bottom tray. Any type of meat can be packaged in trays with absorbent inserts. It is particularly advantageous to package poultry in such trays since poultry exudes relatively large quantities of liquid.

In making extruded foams, other additives may be incorporated such as inorganic fillers, pigments, antioxidants, acid scavengers, ultraviolet absorbers, flame retardants, processing aids, extrusion aids, and the like.

Equivalent average pore size is determined by a liquid intrusion technique. The technique measures liquid uptake through the foam across an applied pressure gradient. The data is analyzed according to the Laplace relationship between the pressure drop and pore radius:

$$\Delta P = 2\gamma \cos\theta/R$$

where $\Delta P$ is the pressure gradient required to introduce a liquid with a surface tension $\gamma$ into a pore of radius R (micrometers) where the contact angle between the liquid and the foam is $\theta$.

Figure 8:
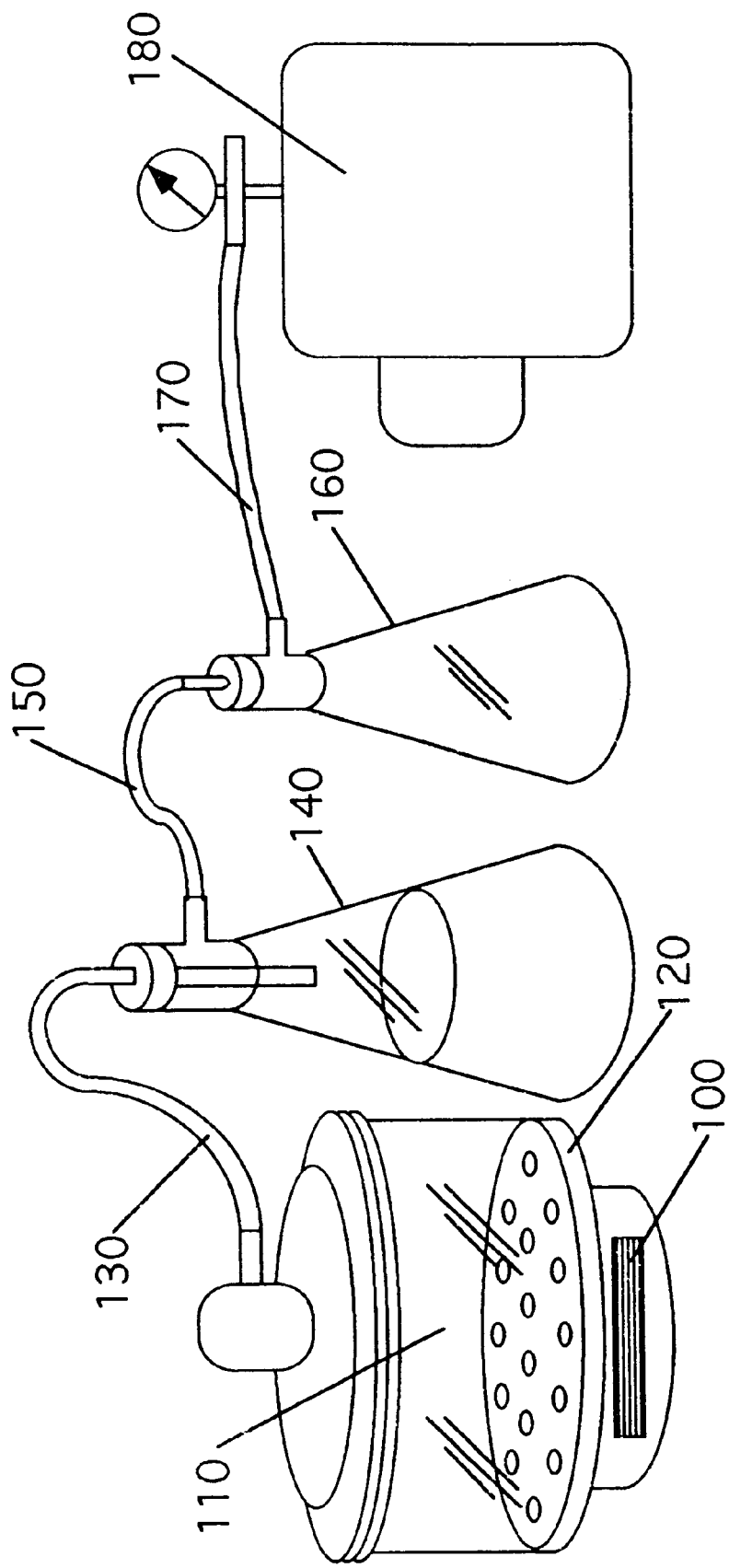
FIG. 8 is a perspective view of an apparatus employed to measure equivalent average pore size.

An apparatus for measuring equivalent average pore size is shown in FIG. 8. A foam sample 100 is placed in the bottom of a desiccator 110 below a desiccator plate 120. Plastic tubing 130 is used to connect desiccator 110 to a first filter flask 140, which functions as a liquid reservoir. Plastic tubing 150 is used to connect first filter flask 140 with a second filter flask 160, which functions as a liquid trap. Plastic tubing 150 is used to connect second filter flask 160 with a vacuum pump 180, which is used to create a pressure gradient through the system or remainder of the apparatus.

Vacuum pump 180 is set to a desired vacuum pressure level and the pressure within the system is allowed to stabilize for a time, approximately 10 minutes. Once system pressure is stable, the end of plastic tube 130 entering flask 140 is inserted into the liquid retained in that flask. Vacuum pump 180 is then turned off, which repressurizes the system and forces liquid from flask 140 into desiccator 110. There must be enough liquid in flask 140 to cover desiccator plate 120. After about 15 minutes, foam sample 100 is removed from the liquid and blotted with a paper towel or other absorbent medium to remove any excess water on its surface. Foam sample 100 is weighed to determine the amount of liquid absorbed. This is repeated for a series of different pressure levels, including essentially full vacuum, recording the amount liquid pickup at each point. The incremental volume absorbed with each change in pressure level (pressure drop) is related to pore size distribution.

Figure 9:
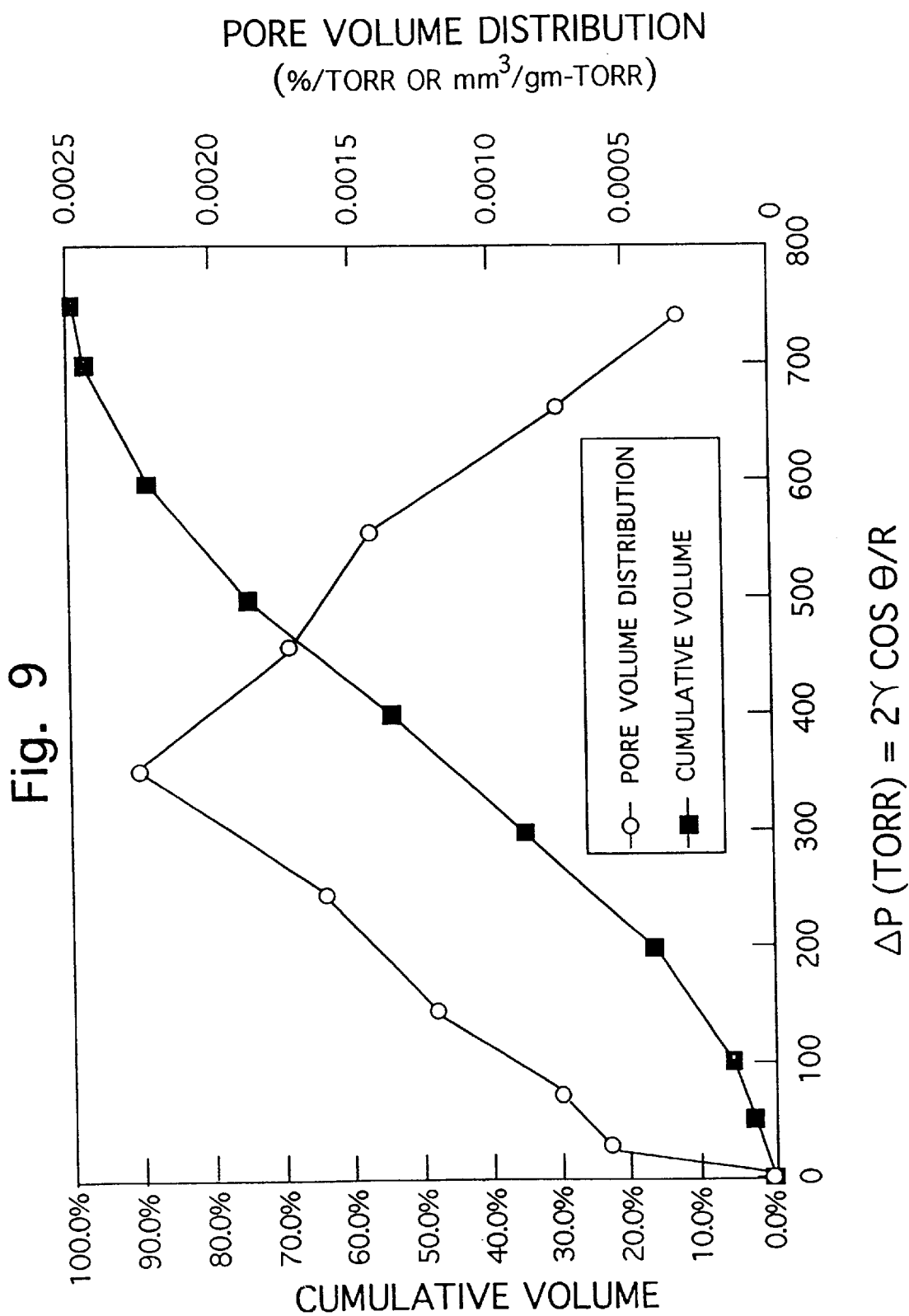
FIG. 9 is a graph of pore volume distribution and cumulative volume absorbed versus pressure drop for a sample data set as can be measured by the apparatus of FIG. 3.

After collecting data for amount of liquid absorbed vs. $\Delta P$ (pressure drop), the pore size distribution can be determined. The pore radius (pore size) corresponding to each $\Delta P$ can be calculated from the Laplace relationship described above. FIG. 9 illustrates a sample data set for the amount of liquid absorbed vs. $\Delta P$. The first derivative of this curve with respect to pore volume (or $\Delta P$) is the pore volume distribution.

If desired, equivalent average pore size may also be determined using an automated porometer, such as the Perm Porometer 200 PSI by PMI (Porous Materials, Inc.) The following are examples of the present invention, and are not to be construed as limiting. Unless otherwise indicated, all percentages, parts, or proportions are by weight.

EXAMPLES

Example 1

Extruded, open-cell polystyrene foams were sulfonated and subsequently tested for absorbency.

The foams were made with a foaming apparatus comprising an extruder, a mixer, a cooler, a die, and forming plates in sequence. Polystyrene resin of 200,000 weight average molecular weight according to size exclusion chromatography (SEM) was fed to the extruder and mixed with talc, graphite, and calcium stearate to form a polymer melt. The polymer melt was fed to the mixer and mixed a blowing agent mixture of 1,1,1,2-tetrafluoroethane, ethyl chloride, and carbon dioxide to form a polymer gel. The polymer gel was cooled to a desirable foaming temperature in the cooler and subsequently conveyed through the die to a region of lower pressure to effect expansion of the extrudate to a foam product. During expansion, the extrudate was elongated downstream of the die by opposing forming plates contacting the extrudate from above and below to reduce foam expansion in the vertical direction and increase foam expansion in the extrusion and horizontal directions.

The foams had an average cell size of 50 micrometers, an equivalent average pore size of 15 micrometers, and an average open cell content of essentially 100 percent. The foams had a thickness of 2 inches (5.1 centimeters (cm)).

The foam was sulfonated by i) exposing it to sulfur trioxide gas by purging for one minute followed by a ten minute reaction time, ii) neutralizing it with aqueous ammonium hydroxide for 1–3 minutes, iii) rinsing it with water, iv) and drying it at an elevated temperature to remove the water. Two different levels of sulfonation were employed. Two foam samples were made at each sulfonation level. One set (Foam #1) of foam samples had an average of 2.3 weight percent sulfur and the other set (Foam #2) had an average of 2.0 weight percent sulfur based on foam weight?. The sulfur concentration was determined by neutron activation energy analysis.

The foams were tested for vertical wicking to determine both amount of liquid absorbed (uptake) and rate of absorption. A sample of foam 6 inches (15.2 cm) in length, 1 inch (2.5 cm) width and ⅛ inch (0.32 cm) thickness was cut out of the middle of the foam in the extrusion direction and subsequently erected vertically. The sample was dipped to a ½ cm liquid depth. Wicking height as a function of time was ascertained.

The liquid absorbed was a synthetic urine composition similar to the JAYCO synthetic urine described in U.S. Pat.

No. 5,260,345. The composition is made by mixing 1.0 gram KCl; 1.0 gram $Na_2SO_4$; 0.42 gram $NH_4H_2PO_4$; 0.07 gram $(NH_4)_2HPO_4$; 0.12 gram $CaCl_2 \cdot 2H_2O$; 0.25 gram $MgCl_2 \cdot 6H_2O$; and 497.14 distilled water. The synthetic urine composition had a surface tension of approximately 72 dynes/centimeter.

The weight of synthetic urine absorbed by the foam (in grams urine per gram of foam) was 20.7 for each of the two samples of Foam #1 and 23.2 for each of the two samples of Foam #2. The theoretical uptake values for these foams was 21.8 and 23.2 grams of urine per gram of foam, respectively, as calculated by theoretical volume available based upon open cell content. Thus, both foams absorbed substantially up to their theoretical volumetric limit of synthetic urine in the vertical wicking test. The time to wick vertically to a height of 6 centimeters was 33 and 28 seconds for the two samples of Foam #1 and 35 and 40 seconds for the two samples of Foam #2.

The percent or urine absorbed based upon theoretical uptake for Foams #1 and #2 was 95 percent and 100 percent, respectively. These absorption levels far exceed those of prior art extruded open cell foams, which typically exhibit absorbency based upon theoretical uptake of only about 15 percent or less.

Example 2

Samples of extruded, open-cell foams similar to those of Example 1 were contacted with an aqueous detergent solution, dried, and subsequently tested for absorbency of synthetic urine.

Four samples of the foam were saturated by vacuum saturation with an aqueous detergent solution of 0.5 weight percent JOY brand dishwashing liquid (Proctor and Gamble) based upon the total weight of the aqueous detergent solution (actual solids in the detergent solution was 0.13 weight percent based on weight of the aqueous solution) and then dried by heating at 80° C. in a forced air oven.

The increase in weight of the foams varied from 0.036 to 0.041 grams with an average of 0.038 grams. This corresponded to the amount of surfactant residue remaining on the surfaces of the foam after drying of the detergent solution. This also corresponded to 3.59 percent to 4.05 percent with an average of 3.76 percent surfactant residue based upon the weight of the foam.

The foams were subjected to the vertical wicking test as in Example 1. The weight of synthetic urine (in grams) absorbed by the foams (in grams) in a vertical wicking test varied from 21.8 to 22.4 for an average of 22.0. This compares favorably to an average of 24.4 grams of aqueous detergent solution absorbed per gram of foam during vacuum saturation during initial preparation of the foam samples. Wicking time (rate) vertically to a height of 6 cm for the four foams varied from 112 to 160 seconds.

Absorption performance was excellent. The percent of urine absorbed based upon theoretical uptake for Foams #1 and #2 was 90 percent and 92 percent, respectively.

Example 3

Extruded, open cell polystyrene foams were prepared and tested for absorbency of a detergent solution.

The foams were prepared with the apparatus disclosed in Example 1. Process conditions and foam physical properties are disclosed in Tables 1 and 2. The polystyrene resin (PS) employed was 135,000 weight average molecular weight according to size exclusion chromatography. The Kraton G 1657 resin was an SEBS copolymer (styrene/ethyl benzene/styrene) having 13 percent styrene monomeric content by weight and has a structure which is 65 percent linear and 35 percent diblock by weight. The HF 1030 ethylene polymer was an ethylene/octene copolymer sold under the tradename INSITE by The Dow Chemical Company. The HF1030 had a density of 0.935 grams/cubic centimeter, a melt index of 2.5, and a melt temperature of 125° C.

The liquid absorbed was an aqueous detergent solution of 1.5 weight percent JOY brand dishwashing liquid (Proctor and Gamble) based upon the total weight of the aqueous detergent solution (actual solids in the detergent solution was 0.75 weight percent based on weight of the aqueous solution). The foams were subject to the vertical wicking test described in Example 1.

TABLE 1

| Run # | Polymer(s) (weight proportions) | Blowing Agent (pph) | Additive | Tf (° C.) |
|---|---|---|---|---|
| 1 | PS | $CO_2$/EtCl/134a (2.4/1.8/2.8) | 0.8 pph talc | 141 |
| 2 | PS/Kraton G (90/10) | $CO_2$/EtCl (2.4/3.2) | 0.8 pph talc | 143 |
| 3 | PS/Kraton G (90/10) | $CO_2$/EtCl/134a (2.4/1.8/2.8) | 0.8 pph talc | 140 |
| 4 | PS/HF1030 (87/13) | $CO_2$/EtCl/134a (2.4/1.8/2.8) | 0.8 pph talc | 143 |

$CO_2$ — Carbon Dioxide
EtCl — Ethyl Chloride
134a — 1,1,1,2-tetrafluorethane
pph — Parts per hundred parts polymer by weight
Tf — Foaming Temperature

TABLE 2

| Run #1 | O. C. Content (Percent) | Cell Size (micrometers) | E. A. P. S. (micrometers) | Density pcf (kg/m³) | V. W. H. (centimeters) | Wicking Time (Seconds) | Theoretic 1 Uptake (Percent) |
|---|---|---|---|---|---|---|---|
| 1 | 93 | 220 | — | 2.62 (41.9) | 4.5 | 110 | 98 |
| 2 | 92 | 420 | 50 | 3.7 (59.2) | 3.5 | 143 | 86 |

TABLE 2-continued

| Run #1 | O. C. Content (Percent) | Cell Size (micro- meters) | E. A. P. S. (micro- meters) | Density pcf (kg/m³) | V. W. H. (centi- meters) | Wicking Time (Seconds) | Theoretic 1 Uptake (Percent) |
|---|---|---|---|---|---|---|---|
| 3 | 97 | 510 | — | 2.8 (44.8) | 2.5 | 124 | 86 |
| 4 | 93 | 260 | — | 4.0 (64.0) | 6.0 | 178 | 88 |

O. C. Content — Open Cell Content
E. A. P. S. — Equivalent Average Pore Size
V. W. H. — Vertical Wicking Height
PCF — Pounds Per Cubic Foot As seen from Table 2, absorption performance was good even with foams of relatively large cell sizes.

While embodiments of the foam and the methods of the present invention have been shown with regard to specific details, it will be appreciated that depending upon the manufacturing process and the manufacturer's desires, the present invention may be modified by various changes while still being fairly within the scope of the novel teachings and principles herein set forth.

What is claimed is:

1. A method of absorption, comprising contacting a liquid and an extruded, open-cell thermoplastic foam, the foam having a structure substantially of cell walls and cell struts, the foam having an overall open-cell content of about 50 percent or more, the foam having an average cell size of up to about 1.5 millimeters, the foam has liquid absorbing capacity which is about 50 percent or more of its theoretical volume capacity.

2. The method of claim 1, wherein the foam has an equivalent average pore size of about 5 micrometers or more.

3. The method of claim 1, wherein the foam has an equivalent average pore size of about 10 micrometers or more.

4. The method of claim 1, wherein the foam has liquid absorbing capacity which is about 70 percent or more of its theoretical volume capacity.

5. The method of claim 1, wherein the foam has liquid absorbing capacity which is about 90 percent or more of its volume capacity.

6. The method of claim 1, wherein the thermoplastic material compromises greater than 50 percent or more by weight alkenyl aromatic monomeric units.

7. The method of claim 1, wherein the foam loses 10 percent or less of its retained liquid when exposed to a pressure of 210 kilopascals.

8. The method of claim 2, wherein the thermoplastic foam is a polystyrene foam, the polystyrene being a weight average molecular weight of about 125,000 to about 300,000.

9. The method of claim 2, wherein the thermoplastic foam is a polystyrene foam, the polystyrene being a weight average molecular weight of about 165,000 to about 200,000.

10. The method of claim 1, wherein the overall open-cell content is about 90 percent or more.

11. The method of claim 1, wherein the overall open-cell content is about 95 percent or more.

12. The method of claim 1, the foam having an equivalent average pore size of about 15 micrometers or more.

13. The method of claim 1, wherein the foam has an average cell size of from about 0.01 to about 1.0 millimeter.

14. The method of claim 1, wherein the foam has an average cell size of from about 0.01 to about 0.07 millimeters.

15. The method of claim 1, wherein a portion or a substantial portion of the internal cell surfaces have a surfactant deposited thereon.

16. The method of claim 1, wherein a portion or a substantial portion of the internal cell surfaces are sulfonated.

17. The method of claim 1, wherein the foam is a sheet foam of less than 0.375 inch (0.95 cm) in thickness.

18. The method of claim 1, wherein the foam is a plank foam having a thickness of 0.375 inches (0.95 cm) or more.

19. The method of claim 1, wherein the density of the foam is from about 16 to about 250 kg/cubic meter.

20. The method of claim 1, wherein the density of the foam is from about 25 to about 100 kg/cubic meter.

21. The method of claim 1, wherein the foam has an average cell size in one dimension which is about 25 percent or more larger than the average cell size in either or both of the other two dimensions.

22. The method of claim 1, wherein the foam has an average cell size in one dimension which is about 50 percent or more larger than the average cell size in either or both of the other two dimensions.

23. The method of claim 1, wherein the foam has an equivalent average pore size of about 5 micrometers or more, the foam having liquid absorbing capacity which is about 70 percent or more of its theoretical volume capacity, the foam having an overall open-cell content is about 90 percent or more, the foam having a density of from about 16 to about 250 kg/cubic meter, the thermoplastic material comprising greater than 50 percent or more by weight alkenyl aromatic monomeric units, the foam having an average cell size of up to about 0.01 to about 1.0 millimeter.

24. The method of claim 23, wherein the thermoplastic foam is a polystyrene foam, the polystyrene having a weight average molecular weight of about 125,000 to about 300,000.

25. The method of claim 23, wherein the thermoplastic foam is a polystyrene foam, the polystyrene having a weight average molecular weight of about 165,000 to about 200,000.

26. The method of claim 1, wherein the foam has an equivalent average pore size of about 10 micrometers or more, the foam being capable of absorbing about 90 percent or more of its theoretical volume capacity, the foam having an overall open-cell content is about 90 percent or more, the foam having a density of from about 25 to about 100 kg/cubic meter, the thermoplastic material comprising greater than 50 percent or more by weight alkenyl aromatic monomeric units, the foam having an average cell size of up to about 0.01 to about 0.07 millimeter.

27. The method of claim 26, wherein the foam The method of claim 2, wherein the thermoplastic foam is a polystyrene foam, the polystyrene having a weight average molecular weight of about 125,000 to about 300,000.

28. The method of claim 26, wherein the thermoplastic foam is a polystyrene foam, the polystyrene having a weight average molecular weight of about 165,000 to about 200,000.

29. A process for making an extruded open-cell thermoplastic foam of about 50 percent or more open cell content, the process comprising extruding and expanding an expandable thermoplastic gel comprising a mixture of a thermoplastic material and a blowing agent out of an extrusion die to form an expanding extrudate which expands to form the foam, the improvement being elongating the extrudate as it exits the extrusion die and expands to an extent sufficient to make the average cell size about 25 percent or more larger in the dimension of elongation than the average cell size in either or both of the other dimensions.

30. The process of claim 29, wherein the extrudate is elongated by stretching in the extrusion direction.

31. The process of claim 29, wherein the extrudate is elongated by stretching in the transverse direction.

32. The process of claim 29, wherein the extrudate is elongated in the extrusion direction by pressure from forming plates contacting opposing surfaces of the extrudate downstream of the die.

33. The process of claim 29, wherein the extrudate is elongated in the extrusion direction by opposing nip rollers downstream of the extrusion die.

34. The process of claim 29, wherein the extrudate is elongated to an extent sufficient to make the average cell size about 50 percent or more larger in the dimension of elongation than the average cell size in either or both of the other dimensions.

35. The method for enhancing the absorbency of an open cell thermoplastic foam, comprising: a) providing the foam, b) applying a surfactant to an exposed surface of the foam whereby the surfactant remains at the surface and does not infiltrate a substantial distance into the foam.

36. The method of claim 29, wherein the surfactant is applied in a solution form and subsequently permitted to dry to leave a residue on the exposed surface.

37. The method of claim 29, wherein the foam is dried by exposure to heat.

38. The method of claim 29, wherein the foam is an extruded thermoplastic foam.

39. A meat tray capable of receiving and retaining meat therein, the meat tray comprising a tray and an insert, the insert comprising an extruded, open-cell thermoplastic foam and tray positioned within the tray, the foam having an open cell content of about 50 percent or more, the foam being an average cell size of up to about 1.5 millimeters, the foam being a structure of substantially cell walls and struts, the foam having liquid absorbing capacity which is about 50 percent or more of its theoretical volume capability, the foam has a thickness of less than 0.375 inch (0.95 cm).

40. The meat tray of claim 39, wherein the foam has an equivalent average pore size of about 5 micrometers or more, the foam having liquid absorbing capacity which is about 70 percent or more of its theoretical volume capacity, the foam having an overall open-cell content is about 90 percent or more, the foam having a density of from about 16 to about 250 kg/cubic meter, the thermoplastic material comprising greater than 50 percent or more by weight alkenyl aromatic monomeric units, the foam having an average cell size of up to about 0.01 to about 1.0 millimeter.

41. The meat tray of claim 40, wherein the thermoplastic foam is a polystyrene foam, the polystyrene having a weight average molecular weight of about 125,000 to about 300,000.

42. The meat tray of claim 39, wherein the thermoplastic foam is a polystyrene foam, the polystyrene having a weight average molecular weight of about 135,000 to about 200,000.

43. The meat tray of claim 39, wherein the foam has an equivalent average pore size of about 10 micrometers or more, the foam having liquid absorbing capacity which is about 90 percent or more of its theoretical volume capacity, the foam having an overall open-cell content is about 90 percent or more, the foam having a density of from about 25 to about 100 kg/cubic meter, the thermoplastic material comprising greater than 50 percent or more by weight alkenyl aromatic monomeric units, the foam having an average cell size of up to about 0.01 to about 0.07 millimeter.

44. The meat tray of claim 42, wherein the foam wherein the thermoplastic foam is a polystyrene foam, the polystyrene having a weight average molecular weight of about 125,000 to about 300,000.

45. The meat tray of claim 42, wherein the thermoplastic foam is a polystyrene foam, the polystyrene having a weight average molecular weight of about 135,000 to about 200,000.

46. A diaper for bodily use, the diaper comprising a flexible sheet foam, the foam having an open cell content of about 50 percent or more, the foam being an average cell size of Lup to about 1.5 millimeters, the foam being a structure of substantially cell walls and struts, the foam having liquid absorbing capacity which is about 50 percent or more of its theoretical volume capability.

\* \* \* \* \*